United States Patent [19]

Ohnuma et al.

[11] Patent Number: 5,036,055
[45] Date of Patent: Jul. 30, 1991

[54] ACYLATED DERIVATIVES OF ETOPOSIDE

[75] Inventors: Takeshi Ohnuma, Tokyo; Rika Obata, Kamakura; Hideo Kamei, Tokyo; Takayuki Naito, Kawasaki, all of Japan

[73] Assignee: Bristol-Myers Company, New York, N.Y.

[21] Appl. No.: 362,555

[22] Filed: Jun. 7, 1989

[51] Int. Cl.$^5$ .................. A61K 31/70; C07H 15/00
[52] U.S. Cl. ...................... 514/27; 536/4.1; 536/18.1; 536/17.1
[58] Field of Search .............. 536/17.1, 18.1, 18.2, 536/4.1, 117; 514/27, 35

[56] References Cited

U.S. PATENT DOCUMENTS

| | | | |
|---|---|---|---|
| 3,524,844 | 8/1970 | Keller-Juslen | 536/18.1 |
| 4,564,675 | 1/1986 | Kurabayashi et al. | 536/18.1 |
| 4,567,253 | 1/1986 | Durst et al. | 536/18.1 |
| 4,716,221 | 12/1987 | Umezawa et al. | 536/17.2 |
| 4,853,467 | 8/1989 | Vyas et al. | 536/17.9 |
| 4,868,291 | 9/1989 | Saulnier et al. | 536/18.1 |
| 4,874,851 | 10/1989 | Vyas et al. | 536/17.2 |
| 4,888,419 | 12/1989 | Saulnier et al. | 536/18.1 |
| 4,912,204 | 3/1990 | Ohnuma et al. | 536/18.1 |
| 4,916,217 | 4/1990 | Saulnier et al. | 536/17.1 |

FOREIGN PATENT DOCUMENTS

| | | |
|---|---|---|
| 956939 | 10/1974 | Canada . |
| 0162701 | 11/1985 | European Pat. Off. . |
| 0226202 | 6/1987 | European Pat. Off. . |
| 0304086 | 2/1989 | European Pat. Off. . |
| 0305972 | 3/1989 | European Pat. Off. . |
| 0320988 | 6/1989 | European Pat. Off. . |
| 1518706 | 3/1968 | France . |
| 219196 | 12/1983 | Japan . |
| 225096 | 12/1983 | Japan . |
| 61-134396 | 6/1986 | Japan . |
| 63-150293 | 6/1988 | Japan . |
| 63-192793 | 8/1988 | Japan . |
| 6617379 | 6/1967 | Netherlands . |
| 2207674 | 2/1989 | United Kingdom . |
| 8600018 | 1/1986 | World Int. Prop. O. . |

OTHER PUBLICATIONS

Yamashita, K., et al., "Measurement of Plasma Etoposide by Radio Immunoassay", *Journal of Pharm. & Biomed. Anal.*, 5(1):11-20.

*Primary Examiner*—Johnnie R. Brown
*Assistant Examiner*—Nancy S. Carson
*Attorney, Agent, or Firm*—Mollie M. Yang

[57] ABSTRACT

The epipodophyllotoxin glucosides disclosed are acylated at herein one or both sugar hydroxyl groups. These compounds exhibit significant activity against P388 murine leukemia.

12 Claims, No Drawings

ACYLATED DERIVATIVES OF ETOPOSIDE

BACKGROUND OF THE INVENTION

1. Field of the Invention

The present invention relates to derivatives of epipodophyllotoxin, their use as antitumor agents, and pharmaceutical compositions containing them. More particularly, the novel compounds of the present invention are acyl derivatives of 4'-demethylepipodophyllotoxin glucosides.

2. Description of Background Art

Etoposide and teniposide are clinically useful antitumor agents derived from the naturally occurring lignan, podophyllotoxin. Currently etoposide is marketed in the United States under the trade name Vepesid for the treatment of small cell lung cancer and testicular cancer. The favorable pharmacological properties of etoposide and teniposide have encouraged much activity in the search for other active analogs within the same class.

4'-0-Demethylepipodophyllotoxin glucosides wherein the hydroxyl groups of the sugar moiety are acylated have been reported in the literature as intermediates for the preparation of the corresponding 4'-demethylepipodophyllotoxin glucosides; however, the phenol group of these compounds are also protected.

Canadian Patent No. 956,939 discloses compounds of formula (I)

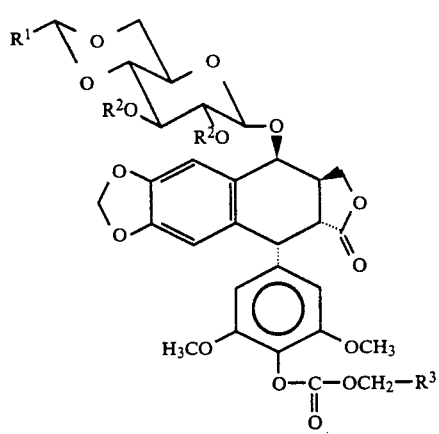

wherein $R^1$ is $C_{1-5}$ alkyl; $R^2$ is acetyl or formyl; and $R^3$ is phenyl or substituted phenyl; possible substituted phenyls mentioned but not exemplified are p-nitrophenyl and p-methoxyphenyl.

U.S. Pat. No. 4,564,675 discloses compounds of the formula (II)

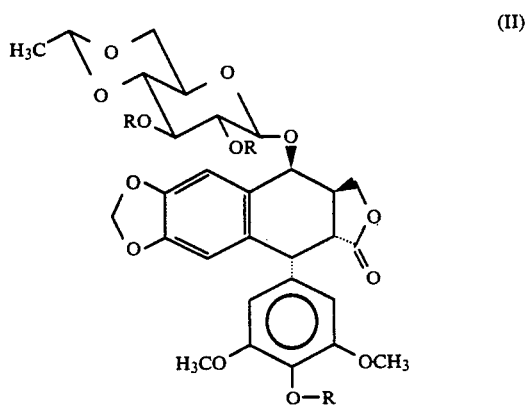

wherein R is $-C(O)CH_2X$, X is a halogen atom.

European Patent Application 162,701 discloses compounds of formula (III)

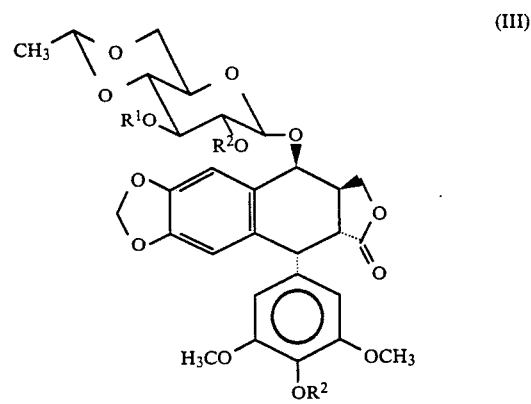

Wherein $R^1$ and $R^2$ may be the same or different and each represent $-C(O)CHX_2$ or $-C(O)CX_3$ wherein X is a halogen atom.

Japanese Kokai 58/225,096 (Derwent Abst. No. 84-034268/06) and 58/219,196 (Derwent Abst. No. 84-027495/05) disclose compounds of formula (IV) and (V), respectively.

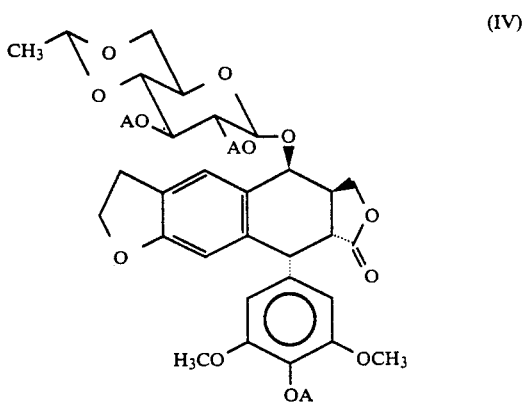

-continued

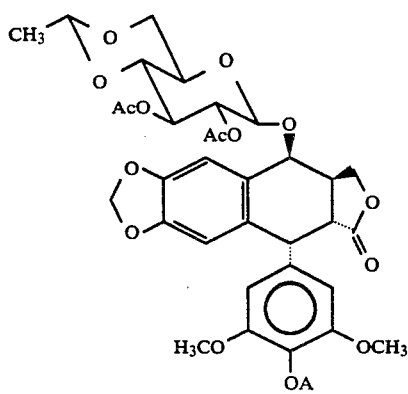

(V)

wherein A stands for —CO₂—CH₂—C(H)m(X)n wherein X is a halogen atom and m is 0 to 2 and n is 1 to 3, m+n=3, and Ac is acyl.

European Patent Application 226,202 discloses an intermediate for etoposide synthesis having the formula (VI)

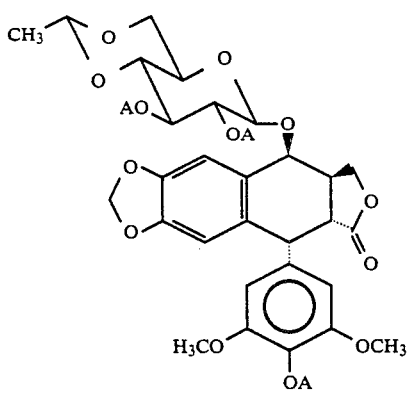

(VI)

wherein A represents an acetyl group.

Mono-hemisuccinate derivatives of etoposide having the formulas (VII) are reported in J. Pharm. Biomed. Anal., 1987, 5(1):11-20

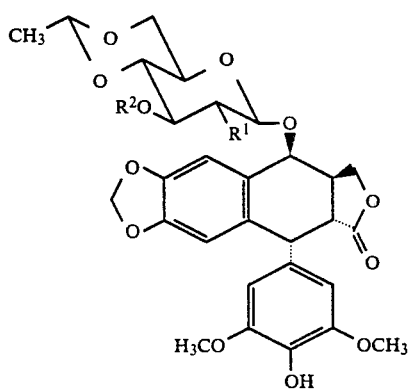

(VII)

wherein one of $R^1$ and $R^2$ is H and the other is —CO(CH₂)₂CO₂H. These compounds are used as a means to conjugate etoposide to bovine serum albumin.

4'-Phosphate of etoposide and the disodium salt thereof are disclosed in Japanese Kokai 63/192,793.

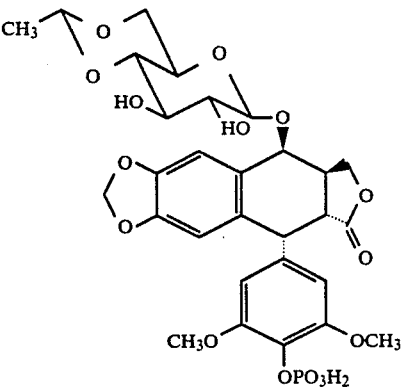

Etoposide phosphate

SUMMARY OF THE INVENTION

The present invention provides compounds having the formula (VIII)

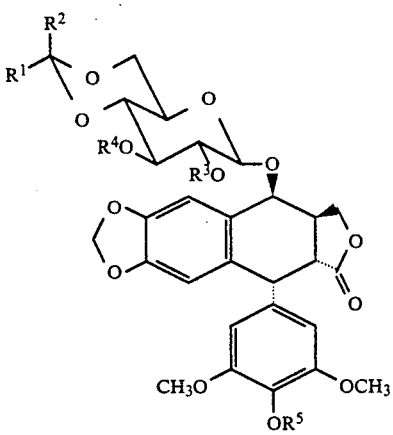

(VIII)

wherein $R^2$ is H and $R^1$ is selected from the group consisting of ($C_{1-10}$)alkyl, ($C_{2-10}$)alkenyl, ($C_{5-6}$)cycloalkyl, 2-furyl, 2-thienyl, ($C_{6-10}$)aryl, and ($C_{7-14}$)aralkyl; or $R^1$ and $R^2$ are each ($C_{1-10}$)alkyl; or $R^1$, $R^2$ and the carbon to which they are attached together represent ($C_{5-6}$)cycloalkyl; one of $R^3$ and $R^4$ is H and the other is selected from the group consisting of ($C_{1-5}$)alkanoyl and benzoyl; or $R^3$ and $R^4$ are the same and are selected from the group consisting of ($C_{1-5}$) alkanoyl and benzoyl; $R^5$ is H or a phosphate group.

Another aspect of the present invention provides pharmaceutical compositions comprising an antitumor effective amount of a compound of formula (VIII) and a pharmaceutically acceptable carrier.

Yet a further aspect of the present invention provides a method for inhibiting tumor growth in a tumor bearing mammalian host which comprises administering to said host an antitumor amount of a compound of formula (VIII).

DETAILED DESCRIPTION OF THE INVENTION

A preferred embodiment of compounds of formula (VIII) comprises those compounds wherein $R^2$ is H and $R^1$ is selected from the group consisting of methyl, 2-thienyl, and phenyl, with methyl being the most preferred substituent.

A further preferred embodiment provides compounds of formula (VIII) wherein $R^3$ and $R^4$ are each $(C_{1-5})$alkanoyl; a most preferred embodiment provides compounds of formula (VIII) wherein $R^3$ and $R^4$ are each a formyl group.

Yet a further preferred embodiment provides compounds of formula (VIII) wherein one of $R^3$ and $R^4$ is H, and the other is $(C_{1-5})$alkanoyl or benzoyl.

As used herein, the term "phosphate" includes the group -$PO_3H_2$ and pharmaceutically acceptable salts thereof. Pharmaceutically acceptable salts include both monobasic and dibasic salts wherein the cation includes, but are not limited to, alkali metals, e.g. sodium, potassium and lithium; alkaline earth metals, e.g. magnesium, calcium and barium; orgnic amine salts, e.g. ammonium.

The novel compounds of the present invention may be prepared by reacting a 4'-phenol protected 4'-demethylepipodophyllotoxin glucoside of formula (IXa) with the desired carboxylic acid or an acylating equivalent thereof, followed by removal of the phenol protecting group.

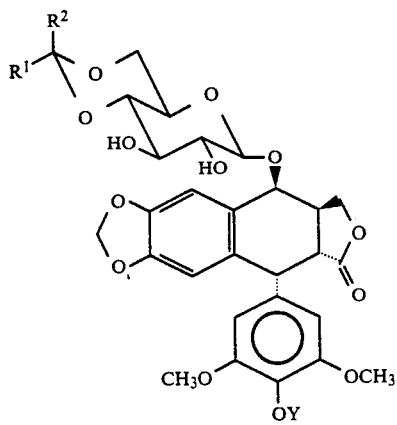

IXa: Y = protecting group
IXb: Y = H

The phenol protecting group is not particularly restricted and may be any that can be introduced and removed with little or no adverse effect on other parts of the molecule. More particularly, the phenol protecting group should be removable by methods that do not disturb the acyloxy functionalities on the sugar moiety of the final products. Methods for phenol protection are well known in the art and as examples of general classes of phenol protecting groups, mention can be made of ethers, acetals, esters, and carbonates. For the purpose of the present invention, we found the benzyloxycarbonyl radical may be conveniently so employed. Thus by reacting a 4'-demethylepipodophyllotoxin glucoside of formula (IXb) with benzylchloroformate at low temperature, e.g. $-15°$ C., in an inert organic solvent such as methylene chloride and in the presence of a tertiary organic base such as pyridine, the corresponding 4'-0-benzyloxycarbonyl-4'-demethylepipodophyllotoxin glucoside is obtained. Compounds of formula (IXb) and their synthesis are disclosed in U.S. Pat. No. 3,524,844.

The acylation of the sugar hydroxyl groups of compounds of formula (IXa) may be effected using the desired carboxylic acid or an acylating agent derived therefrom, for example an acid halide such as acid chloride, active ester derived from N-hydroxysuccinimide or 1-hydroxytriazole, and symmetrical or mixed anhydride. When the carboxylic acid is used as the acylating species, it is preferably used in conjunction with a condensing agent for example a carbodiimide such as dicyclohexylcarbodiimide (DCC). Acylating agents are $C_{1-5}$ alkanoic acids and benzoic acid and acylating equivalents thereof as above described. Alkanoic acids include, but are not limited to, formic acid, acetic acid, propionic acid, butyric acid, pentanoic acid, and branched alkanoic acids such as 2-methylpropionic acid and 3-methylbutanoic acid.

The acylation reaction may be carried out in an inert organic solvent such as pyridine, and preferably include in the reaction mixture an acid acceptor when acid is expected to be a by-product; suitable acid acceptors are for example tertiary amine bases such as pyridine, triethylamine, diisopropylethylamine and the like, or inorganic bases such as sodium and potassium carbonates. The reaction may be conducted at temperatures conducive to formation of the desired products and may be from about $-15°$ C. to about $50°$ C.; the reaction may take several minutes to several days for completion deppending on the nature of the reactants and choice of reaction conditions such as temperature.

The acylation is not regioselective and may result in a mixture of 2''-monoacylated product, 3''-monoacylated product and 2'',3''-bisacylated product. However, when at least two equivalents of the acylating agent is used relative to the epipodophyllotoxin reactant, the bis-acylated derivative is produced predominantly. The proportion of monoacylated product and bisacylated product may be controlled to some extent by manipulative reaction parameters according to principles commonly practiced in the art, e.g. varying the relative amounts of reactants, or varying reaction conditions such as temperature and length of reaction time. In general when equimolar of the reactants are employed, reduced reaction temperature and shorter reaction time tend to increase the amount of monoacylated products formed. Alternatively, monoacylated products may be obtained by first protecting one of the sugar hydroxyl groups of the 4'-phenol protected epipodophyllotoxin glucoside starting material. The protecting group for the sugar hydroxyl group is preferably a bulky protecting group, for example the t-butyldimethylsilyl group, in order to minimize derivatizing both hydroxyl groups. Again, protection of the sugar hydroxyl groups is not regioselective; however, if desired, the 2''-protected or 3''-protected compounds are easily separated chromatographically. We have carried out formylation reactions of etoposide; however, we have not been successful in isolating either of the expected monoformyl derivatives of etoposide.

The product mixture comprising phenol-protected acylated derivatives may be separated into individual components using conventional separation techniques such as column chromatography. Deprotection of the phenolic hydroxyl group and, if necessary, the sugar hydroxyl group provides compounds of the present invention. The deprotection may be effected prior to or subsequent to the isolation of the individual components; the order is not critical. The protecting group is removed by using methods suitable for the protecting group selected and these are generally well known in the art. For example, when the protecting group is benzyloxycarbonyl, it may be removed by catalytic hydrogenation at atmospheric pressure using palladium on carbon as the catalyst; the t-butyldimethylsilyl group may be removed by heating in an aqueous alcoholic solution or by treating with fluoro anion or aqueous acetic acid.

Following the removal of the phenol protecting group, the 4'-phenol group may be further derivatized to provide the 4'-phosphate of formula (VIII). Phosphorylation of the 4'-phenol may be carried out using conventional methods. For example, a compound of formula (VIII) wherein $R^5$ is H may be reacted with a phosphorylating agent such as phosphorous oxychloride; the phosphoryl chloride intermediate is hydrolyzed in situ to give the 4'-phosphate. Hydrolysis in the presence of a base e.g. sodium bicarbonate provides the corresponding salt. This procedure as well as other potentially applicable phosphorylation methods is disclosed in U.S. patent application GB2,207,674 which is hereby incorporated by reference.

It is to be understood that synthesis of compounds of the present invention is not limited to the procedures and reagents outlined above, but may include other methods capable of acylating the hydroxyl groups on the sugar portion of 4'-demethylepipodophyllotoxin glucosides. The reaction conditions will of course vary with the choice of starting materials but may be ascertained by a skilled artisan without undue experimentation.

BIOLOGICAL ACTIVITY

Representative compounds of the present invention were evaluated for antitumor activity against murine transplantable P388 leukemia. Female $CDF_1$ mice were inoculated intraperitoneally with 0.4 ml of diluted ascitic fluid containing $10^6$ lymphocytic leukemia P388 cells. Test compounds were administered intraperitoneally as a single dose on day 1 and animals were observed for 50 days. The percent increase of median survival time (MST) of treated animals over that of untreated control animals was determined and reported as % T/C. Compounds showing % T/C values of 125 or greater are considered to have significant antitumor activity. Table I presents the results of the in vivo evaluation; only the maximum % T/C and the dose giving the maximum effects are reported.

TABLE I

| Antitumor activity against P388 leukemia | | |
|---|---|---|
| Compound | Dose (mg/kg/day) | % T/C MST |
| Example 1 | 30 | 165 |
| Example 3 | 30 | 240 |
| Example 4 | 30 | 210 |
| Etoposide | 30 | 182 |
| Example 6 | 120 | >500 (⅜)* |
| Example 8 | 120 | 145 |
| Example 9 | 60 | 420 (⅛) |
| Example 10 | 120 | 125 |
| Etoposide | 120 | >390 (6/12) |

*Number of survivors/tested on day 50

In vitro cytotoxicity of compounds of the present invention was evaluated against B16-F10 murine melanoma and Moser human colon carcinoma cell lines. Exponentially growing B16-F10 and Moser cells were harvested, counted and suspended in the culture medium at the concentrations of $1.5 \times 10^4$ and $3 \times 10^4$ cells/ml, respectively. Twenty-four hours after planting cell suspension (180 mcl) into wells of a 96-well microtiter plate, test materials (20 mcl) were added to the wells and the plates were incubated for 72 hours. The cytotoxic activities against the tumor cells were colorimetrically determined at 540 nm after staining viable cells with neutral red solution. The results are summarized in Table II.

TABLE II

| In vitro cytotoxicity against murine and human tumor cells IC50 (mcg/ml) | | |
|---|---|---|
| Compound | B16-F10 | Moser |
| Example 3 | 1.6 | 1.1 |
| Example 4 | 1.4 | ND* |
| Example 1 | 1.3 | <0.8 |
| Example 8 | 0.92 | ND |
| Example 9 | 0.17 | 0.83 |
| Example 10 | 4.4 | ND |
| Example 6 | 2.0 | 0.84 |
| Etoposide | 0.45 | ND |

*ND Not determined

Accordingly, the present invention provides a method for inhibiting mammalian tumors which comprises administering an effective tumor-inhibiting dose of an antitumor compound of formula VIII to a tumor bearing host. For this purpose, the drug may be administered by conventional routes including, but not limited to, intravenous, intramuscular, intratumoral, intraarterial, intralymphatic, and oral.

A further aspect of the present invention provides a pharmaceutical composition which comprises a compound of formula VIII and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are for illustrative purposes only and should not be construed as limiting the scope of the invention which is defined solely by the claims appended to the specification.

Preparation of 4'-0-Benzyloxycarbonyl Etoposide (4'-CBZ etoposide)

Benzylchloroformate (1.98 ml, 15 mmol) was added over a period of 30 minutes to a mixture of etoposide (5.88 g, 10 mmol) and pyridine (10 ml) in methylene chloride (100 ml) kept at $-15°$ C. The mixture was stirred at $-15°$ C. for an additional hour, washed successively with 5% HCl, aqueous sodium bicarbonate, and water, and then dried over anhydrous sodium sulfate. The solvent was evaporated to give 8.05 g of the crude product which was purified on a silica gel column (5% methanol-methylene chloride) to give 6.93 g (96%) of 4'-0-benzyloxycarbonyl etoposide as a colorless semi-solid. M.P. 152°–155° C.

IR $\nu_{max}$ (Nujol) cm$^{-1}$: 3200–3600 (OH), 1760 (lactone & 4'-0-benzyloxy carbonyl), 1600 (aromatic).

$^1$H NMR (60 MHz, CDCl$_3$) δ7.36 (5H, s, OCO$_2$CH$_2$Ph), 6.81 (1H, s, 5-H), 6.50 (1H, s, 8-H), 6.25 (2H, s, 2'- and 6'-H), 5.94 (2H, br.s, O-CH$_2$-O), 5.23 (2H, s, -OCO$_2$CH$_2$Ph), 4.89 (1H, d, J=4 Hz, 4-H), 3.66 (6H, s, 3',5'-OC$\overline{H}_3$), 2.8–3.0 (2H, m, 2'',3''-OH,D$_2$O exchanged), 1.38 (3H, d, J=5 Hz, 7''-CH$_3$).

EXAMPLE 1

Preparation of 2'',3''-di-0-acetyl etoposide (VIII, R$^1$=CH$_3$, R$^2$=H, R$^3$=R$^4$=CH$_3$CO—)

(a) Preparation of 4'-0-Benzyloxycarbonyletoposide 2'',3''-di-0-acetate

Acetic anhydride (1 ml) was added to a solution of 4'-CBZ-etoposide (500 mg, 0.69 mmol) in pyridine (10 ml) and the mixture was stirred for 4 hours at room temperature. The reaction mixture was quenched with methanol (2 ml), diluted with dichloromethane, and then washed successively with water, 5% HCl, and water. The organic layer was dried over sodium sulfate, filtered, and the filtrate concentrated in vacuo to obtain a colorless solid (551 mg, 99%). Recrystallization of the crude solid from methanol gave 4'-0-benzyloxycarbonlyetoposide 2'',3''-di-0-acetate as colorless crystals (1st. 395 mg, 2nd. 60 mg). MP 236°–238° C.

IR $\nu_{max}$ (KBr) cm$^{-1}$ 3500(br), 1770, 1610.
UV $\lambda_{max}$ (MeOH) nm (ε) 290 (3950).
Anal. Calcd. for C$_{41}$H$_{42}$O$_{17}$: C 61.04, H 5.25. Found: C 60.64, H 5.36.

(b) Preparation of 2'',3''-di-0-Acetyl etoposide

A stirred solution of the product of step (a) (405 mg, 0.5 mmol) in ethanol-acetone (4:1, 15 ml) was hydrogenated for 1.5 hr in the presence of 10% Pd-C (400 mg) at 1 atm, and then the catalyst was filtered off. The filtrate was concentrated in vacuo to obtain colorless solid (360 mg, ca. 100%), which was recrystallized from ethyl acetate-methanol to give the title compound (204 mg) as colorless crystals. Estimated purity: 90% (by HPLC).

MP 287°–289° C.
IR $\nu_{max}$ (KBr) cm$^{-1}$ 3500(br), 1760, 1610.
UV $\lambda_{max}$ (MeOH) nm (ε) 240(sh, 12780), 285 (4060).
Anal. Calcd. for C$_{33}$H$_{36}$O$_{15}$: C 58.93, H 5.39. Found: C 58.56, H 5.41.

EXAMPLE 2

Preparation of 4'-0-benzyloxycarbonyletoposide 2''-0-acetate and 3''-0-acetate

Acetic anhydride (20 μl, 0.18 mmol) and 4-dimethylaminopyridine (5 mg) were added to a solution of 4'-CBZ etoposide (142 mg, 0.2 mmol) in pyridine (8 ml) kept at −10° C. The mixture was stirred for 30 min. at −10° C., after which time additional acetic anhydride (20 μl, 0.18 mmol) was added. The reaction mixture was stirred for a further 30 min. at −10° C., and then diluted with dichloromethane, and washed successively with water, 5% HCl, aq. sodium bicarbonate, and water. The organic phase was dried over Na$_2$SO$_4$, filtered, and the filtrate was concentrated in vacuo to afford colorless powder (117 mg) containing four components (silica gel TLC: Rf 0.56, 0.46, 0.34 and 0.24; hexane/acetone =1/1). The mixture was separated by silica gel column chromatography (2.5% methanol-dichloromethan). Fractions showing a spot of Rf 0.56 were combined and evaporated in vacuo to give 1 mg (1%) of 2'',3''-di-0-acetyl-4'-0-benzyloxycarbonyletoposide(4). Similarly, fractions of Rf 0.46, 0.34 and 0.24 afforded 3''-0-acetyl-4'-0-benzyloxycarbonyletoposide(3), 2''-0-acetyl-4'-0-benzyloxycarbonyletoposide(2) and 4'-CBZ etoposide (1, 60 mg, 42%) as colorless powder, respectively. Mixtures of 3 and 4 (18 mg), 2 and 3 (15 mg), and 1 and 2 (6 mg) were also obtained from the in-between fractions.

2''-0-acetyl-4'-0-benzyloxycarbonyletoposide

MP 224°–227° C.
IR $\nu_{max}$ (KBr) cm$^{-1}$ 3400(br), 1740, 1600.
UV $\lambda_{max}$ (MeOH) nm (ε) 291 (4200).
Anal. Calcd. for C$_{39}$H$_{40}$O$_{16}$·½H$_2$O: C 61.25, H 5.27. Found: C 60.84, H 5.25.

3''-0-acetyl-4α-0-benzyloxycarbonyletoposide

MP 139°–145° C.
IR $\nu_{max}$ (KBr) cm$^{-1}$ 3500(br), 1770, 1600.
UV $\lambda_{max}$ (MeOH) nm (ε) 291 (3920).
Anal. Calcd. for C$_{39}$H$_{40}$O$_{16}$·½H$_2$O: C 60.54, H 5.34. Found: C 60.27, H 5.26.

EXAMPLE 3

Preparation of 2''-0-acetyl etoposide (VIII, R$^1$=CH$_3$, R$^2$=H, R$^3$=CH$_3$CO—, R$^4$=H)

The procedure described in Example 1, step (b) was followed using 2''-0-acetyl-4'-0-benzyloxycarbonyletoposide (25 mg, 0.03 mmol) to give the title compound (21 mg, ca. 100%) as colorless powder. Estimated purity 90% (by HPLC).

MP 144°–147° C.
IR $\nu_{max}$ (KBr) cm$^{-1}$ 3450(br), 1770, 1740, 1610.
UV $\lambda_{max}$ (MeOH) nm (ε) 240(sh 12900), 284 (4030).
Anal Calcd. for C$_{31}$H$_{34}$O$_{14}$: C 59.04, H 5.43. Found: C 58.65, H 5.46.

EXAMPLE 4

Preparation of 3''-0-acetyl-etoposide (VIII, R$^1$=CH$_3$, R$^2$=H, R$^3$=H, R$^4$=CH$_3$CO)

The procedure described in Example 1, step (b) was followed using 3''-0-acetyl-4'-0-benzyloxycarbonyletoposide (10 mg, 0.01 mmol) to give the title compound (9 mg, ca. 100%) as a colorless powder. Estimated purity: 85% (by HPLC).

MP 226°–228° C.
IR $\nu_{max}$ (KBr) cm$^{-1}$ 3450(br), 1760, 1610.
UV $\lambda_{max}$ (MeOH) nm (ε) 240(sh, 12610), 285 (3960).
Anal. Calcd. for C$_{31}$H$_{34}$O$_{14}$·½H$_2$O: C 58.21, H 5.52. Found: C 58.22/ H 5.42.

EXAMPLE 5

Preparation of 2''-0-acetyletoposide and 3''-0-acetyletoposide from a mixture of 2 and 3

A stirred solution of a mixture of 2 and 3 (60 mg, 0.08 mmol) in ethanol-acetone (4:1, 5 ml) was hydrogenated for 1.5 hr in the presence of 10% Pd-C (30 mg) at 1 atm, and then the catalyst was filtered off. The filtrate was concentrated to give a mixture of regio isomers (50 mg, ca. 100%), which was separated by silica gel column to give 2''-0-acetyletoposide (10 mg, 20%), 3''-0-acetyletoposide (4 mg, 8%), and a mixture of them (30 mg, 61%) as colorless powder.

EXAMPLE 6

Preparation of 2″,3″-di-0-formyl etoposide (VIII; $R^1=CH_3$, $R^2=H$, $R^3=R^4=HCO$—)

a. Preparation of 4′-0-benzyvloxycarbonyletoposide 2″,3″-di-0-formate

To a solution of 4′-CBZ etoposide (100 mg, 0.14 mmol) in pyridine (0.7 ml) was added dropwise a mixture of 99% formic acid (1.4 ml) and acetic anhydride (0.56 ml) at 0° C. The reaction mixture was stirred at room temperature for 4 hours and then diluted with dichloromethane, and washed with water. The organic phase was dried over $Na_2SO_4$, then filtered off, and the filtrate was concentrated in vacuo to obtain colorless solid (122 mg), which was purified by silica gel column ($MeOH:CH_2Cl_2=1:50$) to give 4′-0-benzyloxycarbonyletoposide 2″-3″-di-0-formate (91 mg, 84%) as amorphos powder.

$^1H$ NMR $(CDCl_3)\delta 8.04$ & 7.80 (each 1H, s, CHO), 7.36 (5H, s, $PhCH_2CO$), 6.72 (1H, s, H-5), 6.53 (1H), s, H-8), 6.23 (2H, s, 2′,6′-H), 5.97 (2H, s, $OCH_2O$), 5.23 (2H, s, $PhCH_2)CO$), 5.4–4.0 (9H, m), 3.66 (6H, s, 3′,5′-$OCH_3$), 3.6–2.6 (6H, m), 1.35 (3H, d, J=5 Hz, 8″-$CH_3$)

b. Preparation of 2″,3″-di-0-formyletoposide

A stirred solution of the product of step (a) (71 mg, 0.009 mmol) in ethanol-acetone (4:1, 2.5 ml) was hydrogenated for 1.5 hr in the presence of 10% Pd-C (50 mg) at 1 atm. The catalyst was filtered off and the filtrate was concentrated in vacuo to give the title compound as colorless powder (59 mg, ca. 100%). Estimated purity 80% by HPLC.

MP 278°–280° C.

IR $\nu_{max}$ (KBr) cm$^{-1}$ 3400, 1760, 1740, 1610

UV $\lambda_{max}$ (MeOH) nm ($\epsilon$) 236 (sh, 14,100), 285 (4,230)

$^1H$ NMR $(CDCl_3)\delta 6$ 8.04 & 7.83 (each 1H, s, CHO), 6.72 (1H,s,H-5), 6.53 (1H, s, H-8), 6.23 (2H, s, 2′,6′-H), 5.98 (2H, s, $OCH_2O$), 5.6–4.1 (9H, m), 3.76 (6H, s, 3′,5′-$OCH_3$), 3.7–2.6 (6H, m), 1.35 (3H, d, J=5 Hz, 8″-$CH_3$).

Anal Calcd for $C_{31}H_{32}O_{15}$: C 57.26, H 5.00. Found: C 57.09, H 5.00

EXAMPLE 7

Preparation of 4′-benzyloxycarbonyletoposide 2″-0-benzoate, 3″-benzoate, and 2″,3″-di-0-benzoate Benzoyl chloride (100 μl 0.86 mmol) was added to a solution of 4′-0-CBZ etoposide (500 mg, 0.7 mmol) in pyridine (5 ml). The reaction mixture was stirred at room temperature for 3 days, diluted with dichloromethane, and then washed successively with water, 5% HCl, and water. The organic layer was dried over $Na_2SO_4$, filtered, and the filtrate was concentrated in vacuo to give pale yellow oil, which contained three new components (silia gel TLC: Rf 0.50, 03.8 and 0.21; dichloromethane/methanol=100/1). The mixture was separated by silica gel column chromatography (40% hexane-acetone) to obtain 2″,3″-di-0-benzoate 7 (Rf; 0.50, 30 mg, 5%), 3″-0-benzoate 6 (Rf; 0.38, 227 mg, 40%), 2″-0-benzoate 5 (Rf; 0.21, 70 mg, 12%) and recovered 4′-CBZ etoposide 1 (215 mg, 43%).

4′-Benzyloxycarbonyletoposide 2″-0-benzoate (5)

IR $\nu_{max}$ (KBr) cm$^{-1}$ 3400(br), 1700, 1720, 1600

UV $\lambda_{max}$ (MeOH) nm ($\epsilon$) 281 (4,050)

$^1H$ NMR $(CDCl_3)$ δ7.3–7.9 (10H, m, 2′$C_6H_5$, 5.17 (1H, t, J=8 Hz, 2″-HO, 5.01 (1H, d, J=8 Hz, 1″-H), 4.77 (1H, q, J=5 Hz, 7″-H), 3.2–3.8 (1H, m, 3″-H), 2.75 (1H, br, 3″-OH), 1.31 (3H, d, J=5 Hz, 7″-$CH_3$).

Anal Calcd for $C_{44}H_{42}O_{16}$: C 63.92, H 5.12. Found: C 63.80, H 5.17.

4′-0-Benzyloxycarbonyletoposide 3″-0-benzoate (6)

IR $\nu_{max}$ (KBr) cm$^{-1}$ 3500(br), 1770, 1600

UV $\lambda_{max}$ (MeOH) nm ($\epsilon$) 225 (sh, 30,890), 281 (4,300)

1H NMR $(CDCl_3)$ δ6 7.4–8.0 (10 H, m, 2×$C_6H_5$, 5.34 (1H, t, J=9 Hz, 3″-H, 4.74 (1H, d, J=8 Hz, 1″-H), 4.68 (1H, q, J=5 Hz, 7″-H), 3.60 (1H, m, 2″-H), 1.28 (3H, d, J=5 Hz, 7″-$CH_3$).

Anal Calcd for $C_{44}H_{42}O_{16}$: C 62.55, H 5.25. Found: C 62.73, H 5.29.

4′-0-Benzyloxycarbonyletoposide 2″,3″-di-0-benzoate (7)

IR $\nu_{max}$ (KBr) cm$^{-1}$ 1770, 1730, 1600

UV $\lambda_{max}$ (MeOH) nm ($\epsilon$) 227 (sh, 40,270), 282 (4,550)

$^1H$ NMR $(CDCl_3)$ δ7.3–7.9 (10H, m, 2×$C_6H_5$), 5.55 (1H, t, J=8 Hz, 3″-H), 5.32 (1H, t, J=8 Hz, 2″-H), 4.93 (1H, d, J=8 Hz, 1″-H), 4.50 (1H, q, 7″-H), 1.31 (3H, d, J=5 Hz, 7″-$CH_3$).

Anal Calcd for $C_{51}H_{46}O_{17}$: C 65.80, H 4.55. Found: C 65.28, H 4.98.

EXAMPLE 8

Preparation of 2″-0-benzoyletoposide (VIII, $R^1=CH_3$, $R^2=H$, $R^3=PhCO-$, $R^4=H$)

A stirred solution of 4′-benzyloxycarbonyletoposide 2″-0-benzoate (54 mg, 0.07 mmol) in ethanol-acetone (2′1, 3 ml) was hydrogenated for 2 hours in the presence of 10% palladium on carbon (50 mg) at 1 atm. The catalyst was filtered off and the filtrate was concentrated to give the title compound (40 mg, 88% as colorless powder. Estimated purity 95% by HPLC.

MP 289°–292° C.

IR $\nu_{max}$ (KBr) cm$^{-1}$ 3450, 1760, 1730

UV $\lambda_{max}$ (MeOH) nm ($\epsilon$) 283 (4,470)

$^1H$ NMR $(CDCl_3)$ δ7.4–7.8 (5H, m, $COC_6H_5$), 5.07 (1H, dd, J=7.7 & 9.2 Hz, 2″-H), 4.89 (1H, d, J=7.7 Hz, 1″-H), 4.80 (1H, q, J=5.1 Hz, 7″-H), 4.23 (1H, dd, J=4.8 & 10.3 Hz, 6″-Heq), 3.98 (1H, dt, J=3.3 & 9.2 Hz, 3″-H), 3.64 (1H, t, J=10.3 Hz, 6″-Hax), 3.47 (1H, t, J=9.2 Hz, 4″-H), 3.40 (1H, dt, J=4.8 & 10 Hz, 5″-H), 2.74 (1H, d, J=3.3 Hz, 3″=OH), 1.41 (3H, d, J=5.1 Hz, 7″-$CH_3$).

Anal Calcd for $C_{36}H_{36}O_{14}·H_2O$: C 60.84, H 5.11. Found: C 61.10, H 5.40.

EXAMPLE 9

Preparation of 3″-0-Benzoyletoposide (VIII, $R^1=CH_3$, $R^2=H$, $R^3=H$, $R^4=PhCO$)

According to the procedure of Example 8, 34 mg (0.04 mmol) of 4′-0-benzyloxycarbonyletoposide 3″-0-benzoate was hydrogenated to give the title compound (27 mg, 95%) as colorless solid, which was purified on column chromatography to give colorless crystals. Estimated purity 95% by HPLC.

MP 188°–191° C.

IR $\nu_{max}$ (KBr) cm$^{-1}$ 3400 (br), 1730.

UV $\lambda_{max}$ (MeOH) nm ($\epsilon$) 223 (35,900), 280 (4,030).

$^1H$ NMR $(CDCl_3)$ δ7.4–7.8 (5H, m, COPh), 5.38 (1H, t, J=9.2 Hz, 3″-H), 4.79 (1H, d, J=7.7 Hz, 1″-H), 4.72 (1H, q, J=5.1 Hz, 7″-H), 4.22 (1H, dd, J=5 & 10 Hz, 6″-Heq), 3.67 (1H, brt, J=8 Hz, 2″-H), 3.61 (1H, t, J=10 Hz, 6″-Hax), 3.59 (1H, t, J=9.4 Hz, 4″-H), 3.47

(1H, m, 5"-H), 2.58 (1H, br, 2"-OH), 1.31 (3H, d, J=5.1 Hz, 7"-CH₃).

Anal Calcd for $C_{36}H_{36}O_{14}.2H_2O$: C 59.31, H 4.98. Found: C 59.14, H 5.10.

EXAMPLE 10

Preparation of 2",3"-0-di-benzoyletoposide (VIII, $R^1=CH_3$, $R^2=H$, $R^3=R^4=PhCO-$)

A stirred solution of 4'-0-benzyloxycarbonyletoposide 2",3"-di-0-benzoate (130 mg, 0.14 mmol) in ethyl acetate-ethanol-acetone (4:4:1, 4.5 ml) was hydrogenated according to the procedure of Example 8 to give the title compound (112 mg, ca. 100%) as colorless powder. Estimated purity 90% by HPLC.

MP >295° C.

IR $\nu_{max}$ (KBr) cm$^{-1}$ 1770, 1730.

UV $\lambda_{max}$ (MeOH) nm ($\epsilon$) 226 (sh, 24,200), 281, (3,470).

¹H NMR (CDCl₃) δ7.3-8.0 (10 H, m, 2×COC₆H₅), 5.67 (1H, t, J=9.5 Hz, 3"-H), 5.35 (1H, dd, J=8.1 & 9.7 Hz, 2"-H), 498 (1H, d, J=8.1 Hz, 1"-H), 4.73 (1H, q, J=4.8 Hz, 7"-H), 4.28 (1H, dd, J=4.4 & 10.3 Hz, 6"-Heq), 3.69 (1H, t, J=9.5 Hz, 4"-H), 3.67 (1H, t, J=10 Hz, 6"-Hax), 3.56 (1H, dt, J=9.5 & 10 Hz, 5"-H), 1.33 (3H, d, J=4.8 Hz, 7"-CH₃).

Anal Calcd for $C_{43}H_{40}O_{15}.H_2O$: C 63.39, H 5.20. Found: C 62.99, H 4.99.

EXAMPLE 11

The general procedure described in Example 1 is followed using 4'-CBZ teniposide instead of 4'-CBZ etoposide to provide 2",3"-di-0-acetyl teniposide.

EXAMPLE 12

The general procedure described in Examples 2-4 is repeated using 4'-CBZ teniposide instead of 4'-CBZ etoposide to provide 2"-0-acetyl teniposide and 3"-0-teniposide.

EXAMPLE 13

The general procedure described in Example 6 is repeated using 4'-CBZ teniposide instead of 4'-CBZ etoposide to provide 2",3"-di-0-formyl teniposide.

EXAMPLE 14

The general procedure of Examples 7-10 is repeated using 4'-CBZ teniposide instead of 4'-CBZ etoposide to provide 2"-0-benzoyl teniposide, 3"-0-benzoyl teniposide and 2",3"-di-0-benzoyl teniposide.

What is claimed is:

1. A compound having the formula

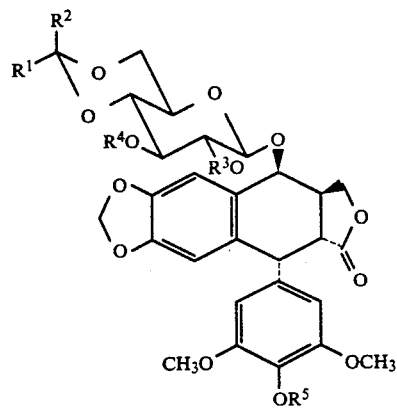

wherein $R^2$ is H and $R^1$ is selected from the group consisting of $C_{1-10}$alkyl, $C_{2-10}$alkenyl, $C_{5-6}$cycloalkyl, 2-furyl, 2-thienyl, $C_{6-10}$aryl, and $C_{7-14}$aralkyl; or $R^1$ and $R^2$ are each $C_{1-10}$alkyl; or $R^1$, $R^2$ and the carbon to which they are attached together represent $C_{5-6}$cycloalkyl; one of $R^3$ and $R^4$ is H and the other is selected from the group consisting of $C_{1-5}$alkanoyl and benzoyl; or $R^3$ and $R^4$ are the same and are selected from the group consisting of $C_{1-5}$ alkanoyl and benzoyl: $R^5$ is H or a phosphate group.

2. A compound of claim 1 wherein $R^2$ is H and $R^1$ is selected from the group consisting of methyl, 2-thienyl and phenyl.

3. A compound of claim 2 wherein $R^1$ is methyl.

4. A compound of claim 1 wherein $R^3$ and $R^4$ are each $(C_{1-5})$alkanoyl.

5. A compound of claim 1 wherein one of $R^3$ and $R^4$ is H, and the other is $(C_{1-5})$alkanoyl or benzoyl.

6. A compound of claim 4 wherein $R^2$ is H and $R^1$ is selected from the group consisting of methyl and 2-thienyl.

7. A compound of claim 6 wherein $R^1$ is methyl, $R^3$ and $R^4$ are both formyl, and $R^5$ is H.

8. A compound of claim 6 wherein $R^1$ is methyl, $R^3$ and $R^4$ are both acetyl, and $R^5$ is H.

9. A compound of claim 3 wherein $R^3$ and $R^4$ are both benzoyl, and $R^5$ is H.

10. The compound of claim 3 wherein $R^5$ is H, one of $R^3$ and $R^4$ is H, and the other is $(C_{2-5})$alkanoyl.

11. The compound of claim 3 wherein $R^5$ is H, one of $R^3$ and $R^4$ is H, and the other is benzoyl.

12. A pharmaceutical composition comprising an antitumor effective amount of a compound of claim 1 and a pharmaceutically acceptable carrier.

* * * * *